United States Patent [19]

Roehr, Jr. et al.

[11] Patent Number: 4,715,520
[45] Date of Patent: Dec. 29, 1987

[54] SURGICAL FASTENER APPLYING APPARATUS WITH TISSUE EDGE CONTROL

[75] Inventors: William H. Roehr, Jr., Ridgefield, Conn.; Richard L. Goodman, White Plains, N.Y.

[73] Assignee: United States Surgical Corporation, Norwalk, Conn.

[21] Appl. No.: 785,992

[22] Filed: Oct. 10, 1985

[51] Int. Cl.$^4$ ............................................. A61B 17/04
[52] U.S. Cl. ................................ 227/19; 227/DIG. 1; 128/334 R; 128/334 C
[58] Field of Search ..................... 128/334 R, 334 C; 227/19, DIG. 1

[56] References Cited

U.S. PATENT DOCUMENTS

| 2,891,250 | 6/1959 | Hirata | 227/19 |
|---|---|---|---|
| 3,247,852 | 4/1966 | Schneider | 128/346 |
| 3,252,643 | 5/1966 | Strekopytov et al. | 227/109 |
| 3,275,211 | 9/1966 | Hirsch et al. | 227/124 |
| 3,494,533 | 2/1970 | Green et al. | 227/19 |
| 3,589,589 | 6/1971 | Akopov | 227/153 |
| 4,354,628 | 10/1982 | Green | 227/19 |
| 4,383,634 | 5/1983 | Green | 227/19 |
| 4,506,671 | 3/1985 | Green | 128/334 R |
| 4,508,253 | 4/1985 | Green | 227/19 |
| 4,513,746 | 4/1985 | Aranyi et al. | 128/334 C |
| 4,522,327 | 6/1985 | Korthoff et al. | 128/334 R |
| 4,527,724 | 7/1985 | Chow et al. | 227/8 |
| 4,530,453 | 7/1985 | Green | 227/DIG. 1 |
| 4,580,712 | 4/1986 | Green | 128/334 R |
| 4,607,636 | 8/1986 | Kula et al. | 227/DIG. 1 |

FOREIGN PATENT DOCUMENTS

| 0101310 | 2/1984 | European Pat. Off. | 128/334 R |
|---|---|---|---|
| 1835500 | 4/1961 | Fed. Rep. of Germany . | |
| 1237035 | 6/1960 | France . | |
| 906791 | 9/1962 | United Kingdom . | |
| 0762869 | 9/1980 | U.S.S.R. | 128/334 R |

OTHER PUBLICATIONS

"Instruments for Suturing the Pulmonary Hilum", Medexport, Moscow, USSR.
P. I. Androsov, "New Surgical Instruments and Their Clinical Use", Medexport, Moscow, USSR.
"Suturing Instruments", Medexport, Moscow USSR.

Primary Examiner—William R. Cline
Assistant Examiner—John K. Ford
Attorney, Agent, or Firm—Kenyon & Kenyon

[57] ABSTRACT

In apparatus for applying a plurality of surgical fasteners to body tissue clamped between fastener holding and anvil parts of the apparatus, tissue edge control members extend into at least one end, and preferably both ends, of the fastener array to prevent any portion of the tissue from extending beyond the ends of the array. This ensures that the fastener array extends completely across the tissue and that no portion of the tissue remains unfastened.

13 Claims, 10 Drawing Figures

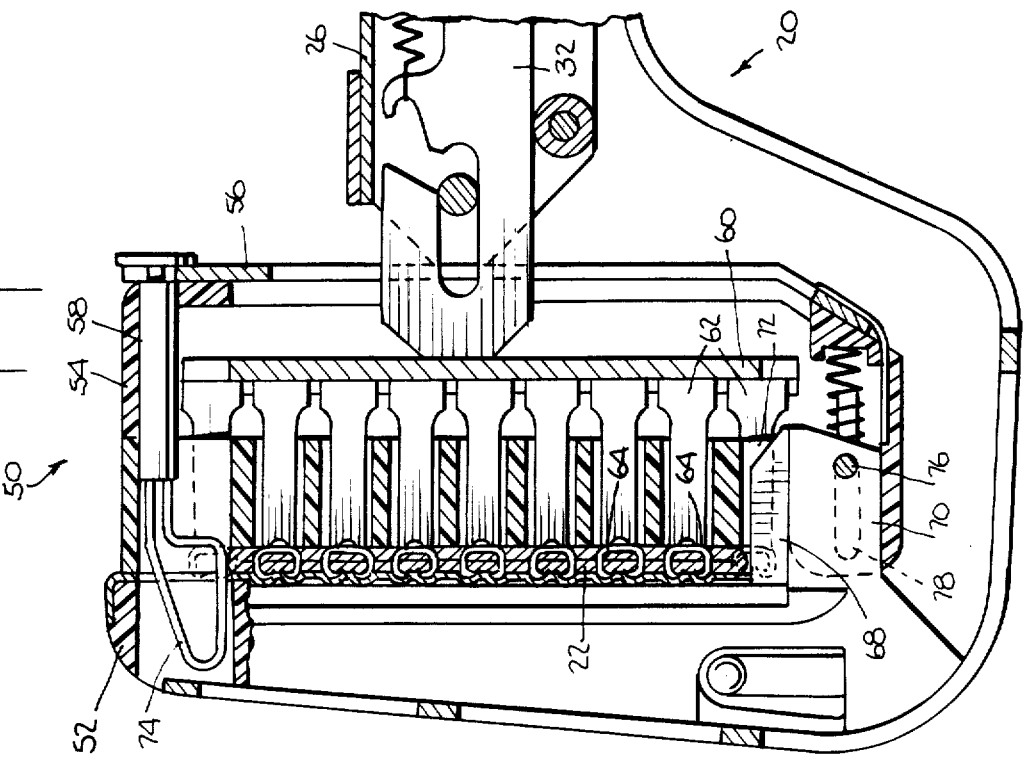
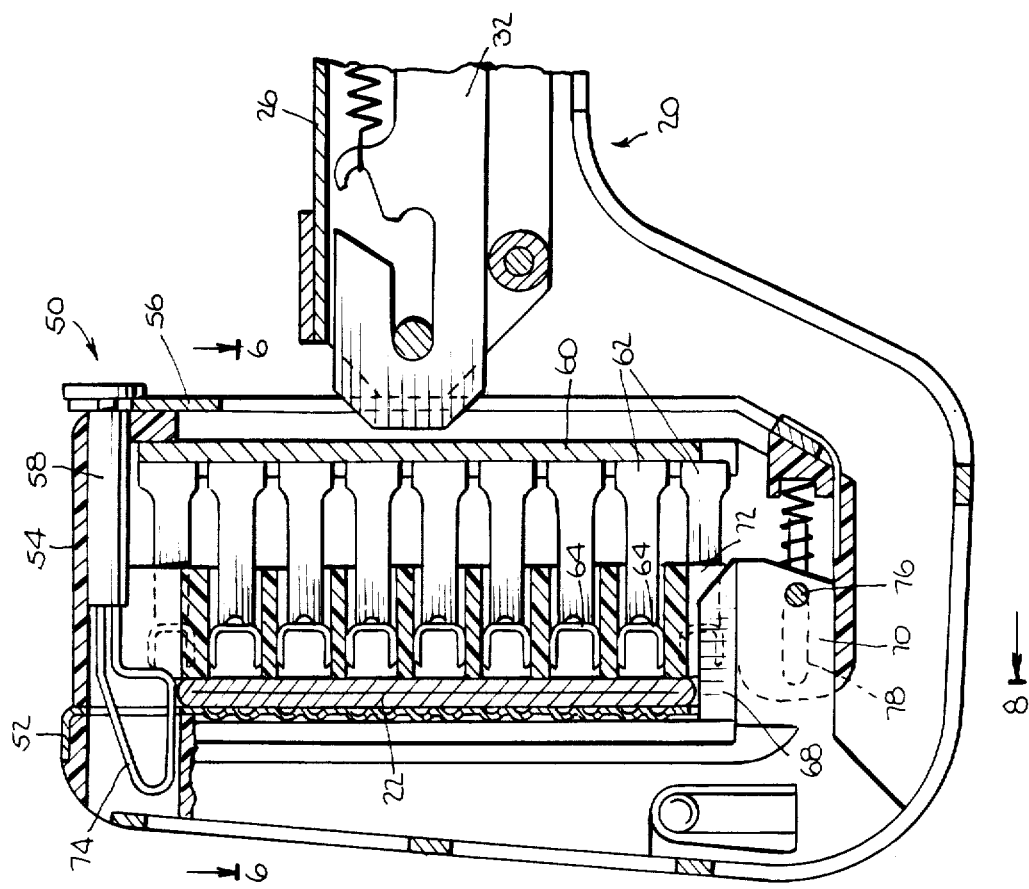

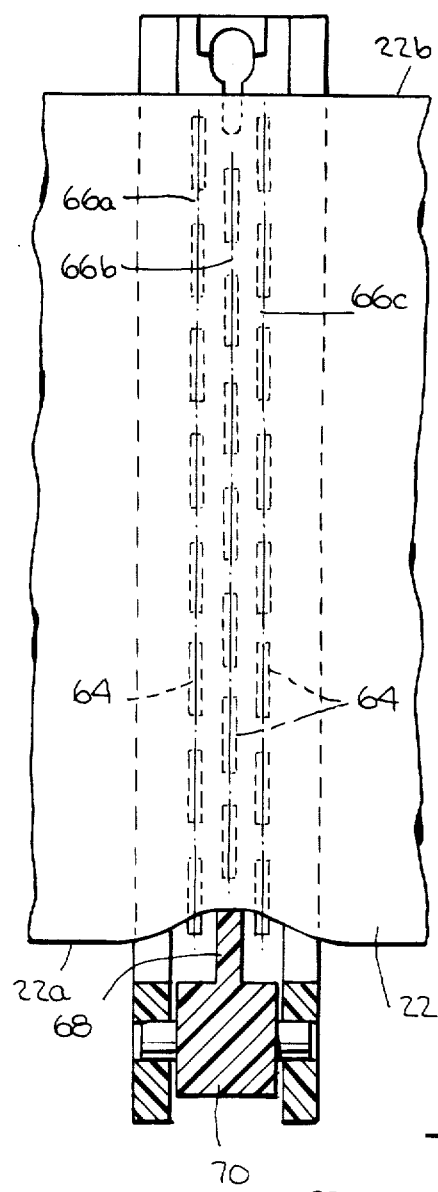
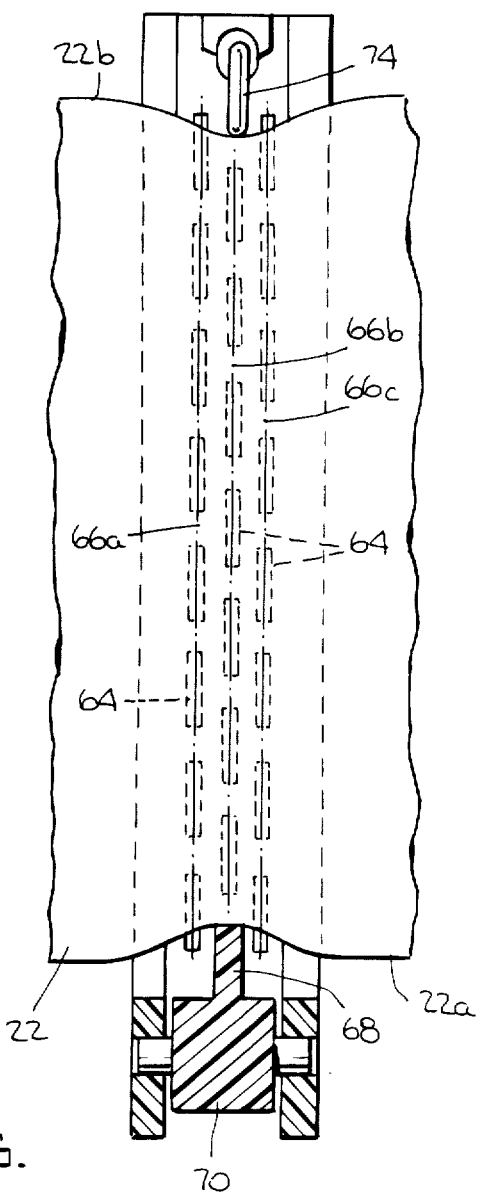
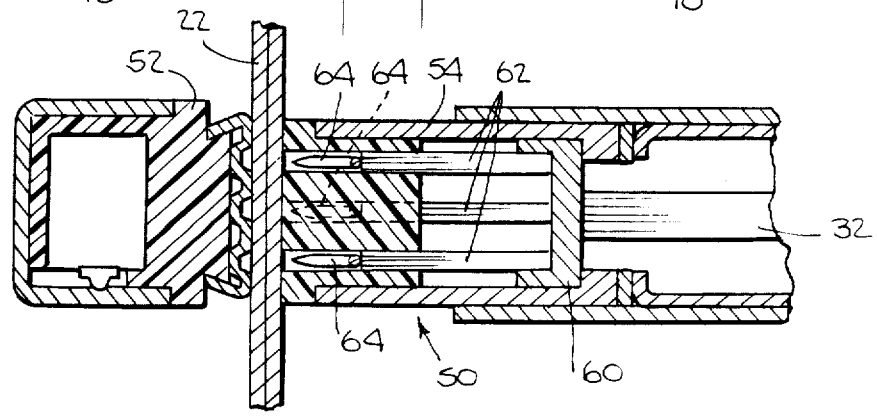

SURGICAL FASTENER APPLYING APPARATUS WITH TISSUE EDGE CONTROL

BACKGROUND OF THE INVENTION

This invention relates to surgical fastener applying apparatus, and more particularly to apparatus for applying a plurality of surgical fasteners in a substantially longitudinal array to body tissue clamped between fastener holding and anvil parts of the apparatus.

Several types of surgical fastener applying devices have been developed for applying a plurality of surgical fasteners in a substantially longitudinal array to body tissue clamped between fastener holding and anvil parts of the apparatus. For example, Hirsch et al. U.S. Pat. No. 3,275,211 shows apparatus for applying two parallel rows of metal surgical staples to body tissue clamped between a staple holding cartridge and the anvil which clinches the staples when they are driven from the cartridge and part way through the tissue. Green U.S. Pat. No. 4,506,671 shows a similar type of instrument in which two-part resinous fasteners are used in place of metal surgical staples. Each two-part fastener includes a fastener part and a retainer part. The fastener parts are driven part way through the tissue so that the ends of the fastener part prongs interlock with the retainer parts which are releasably retained in the anvil part of the apparatus.

As used herein, the term "fastener" is generic to metal staples, two-part resinous fasteners, and the like. Similarly, the term "fastener holding part" is generic to the structure which initially contains metal staples or the fastener parts of two-part resinous fasteners. The term "anvil" is generic to the structure which clinches metal staples or which releasably supports the retainer parts of two-part resinous fasteners.

A number of the known instruments of the type described above have structures for generally confining the tissue to be fastened between the fastener holding and anvil parts of the apparatus. For example, the apparatus shown in the above-mentioned Green patent has a cartridge in which the fastener holding and anvil parts are pivotally connected together adjacent one end of the longitudinal fastener array. Adjacent the other end of the fastener array, a pin extends from the fastener holding part into the anvil when the cartridge is closed. Accordingly, the tissue to be fastened is generally confined between the fastener holding and anvil parts of the apparatus by the pivotal connection adjacent one end of the fastener array and by the pin adjacent the other end of the fastener array.

The above-described tissue confining structures may allow small amounts of tissue to extend beyond the ends of the staple array. In the above-mentioned Green device, for example, a small amount of tissue may remain unfastened between (1) the pivotal connection between the fastener holding and anvil parts of the cartridge, and (2) the adjacent end of the fastener array. Similarly, a small amount of tissue may remain unfastened between the other end of the fastener array and the pin which extends from the fastener holding part into the anvil. In many situations this is not a problem. In some situations, however, it may be desirable to ensure that the fastener array completely traverses the entire tissue structure. For example, this may be important in applying fasteners transversely across a large blood vessel in order to close off the vessel. If even a small portion of the transverse axis of the vessel is left unfastened, there may be unacceptable blood flow past the fastener array.

In view of the foregoing, it is an object of this invention to improve surgical fastener applying apparatus of the type described above by ensuring that the fastener array applied by such apparatus extends completely across the tissue clamped in the apparatus.

It is another object of this invention to ensure that no part of the tissue clamped in surgical fastener applying apparatus of the type described above can remain unfastened.

SUMMARY OF THE INVENTION

These and other objects of the invention are accomplished in accordance with the principles of the invention by providing, in surgical fastener applying apparatus of the type described above, a tissue edge control member adjacent at least one end, and preferably both ends, of the fastener array for ensuring that the adjacent edge of the tissue is inside the associated end of the fastener array. In this way no part of the tissue can remain unfastened.

Further features of the invention, its nature and various advantages will be more apparent from the accompanying drawings and the following detailed description of the invention.

BRIEF DESCRIPTION OF THE DRAWINGS

FIGS. 3-5 are elevational sectional views of the distal portion of the apparatus of FIG. 1 showing successive stages in the operating cycle of the apparatus.

FIG. 6 is a sectional view taken along the line 6—6 in FIG. 4.

FIG. 7 is a sectional view taken along the line 7—7 in FIG. 2.

FIG. 8 is a sectional view taken along the line 8—8 in FIG. 4.

FIGS. 9 and 10 are schematic representations of two alternative embodiments of the invention.

DETAILED DESCRIPTION OF THE INVENTION

Figure 1:
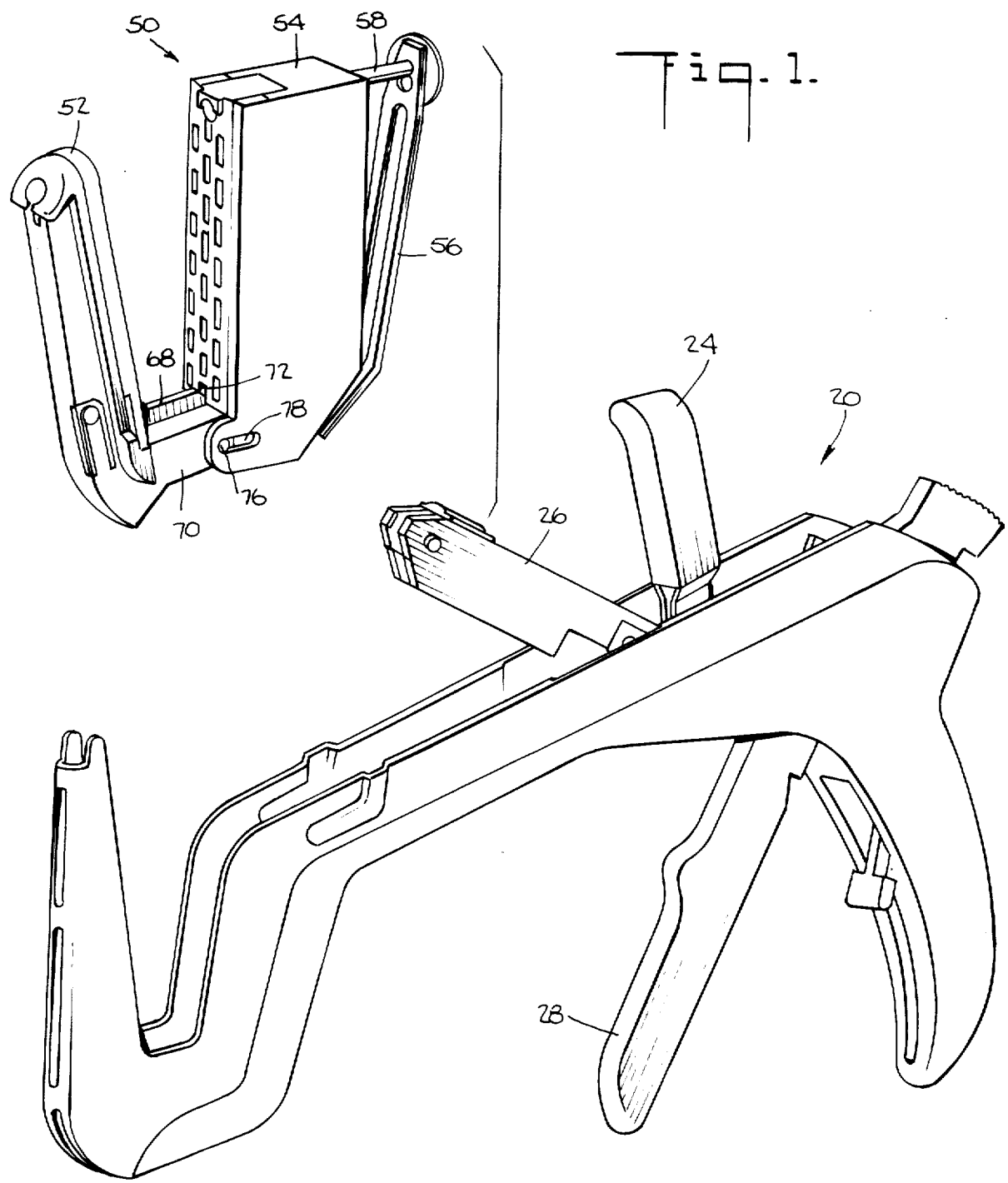
FIG. 1 is a partly exploded perspective view of an illustrative embodiment of the invention.

As shown in FIG. 1, an illustrative embodiment of the invention includes a permanent and reusable actuator 20 for removably receiving and actuating a disposable fastener applying cartridge 50. Actuator 20 may be substantially identical to the actuator shown in FIGS. 1-13 of Green U.S. Pat. No. 4,383,634. Accordingly, actuator 20 will be described only very briefly herein. Although modified in accordance with the present invention, cartridge 50 may also be basically similar to the cartridge shown in the above-mentioned Figures of the Green '634 patent. Again, only the new aspects of cartridge 50 will be described in full detail herein. Reference is also made to U.S. Pat. No. 4,522,327, for a similar actuator.

Figure 2:
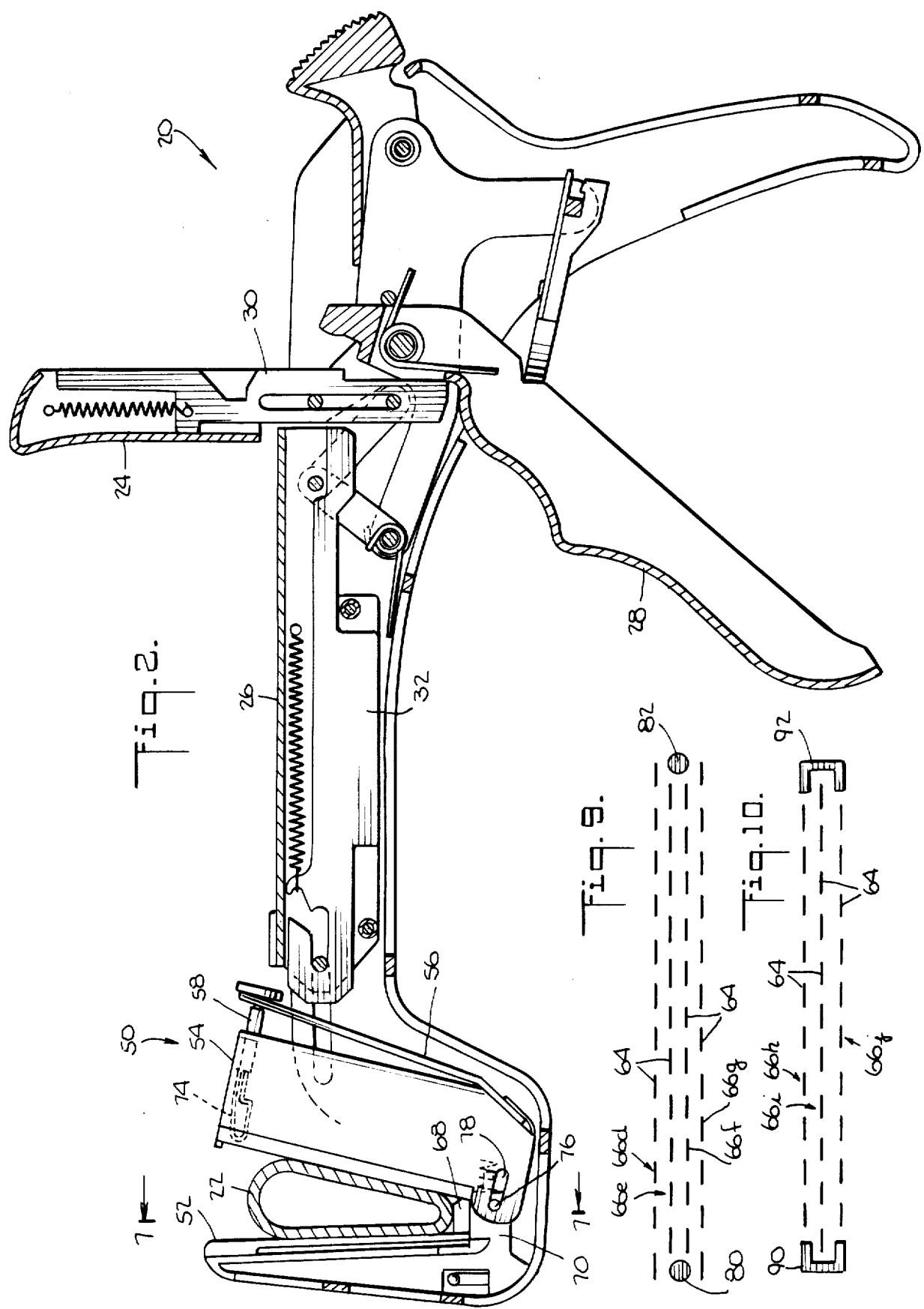
FIG. 2 is an elevational view, partly in section, of the apparatus of FIG. 1 showing an early stage in the operating cycle of the apparatus.
Figure 3:
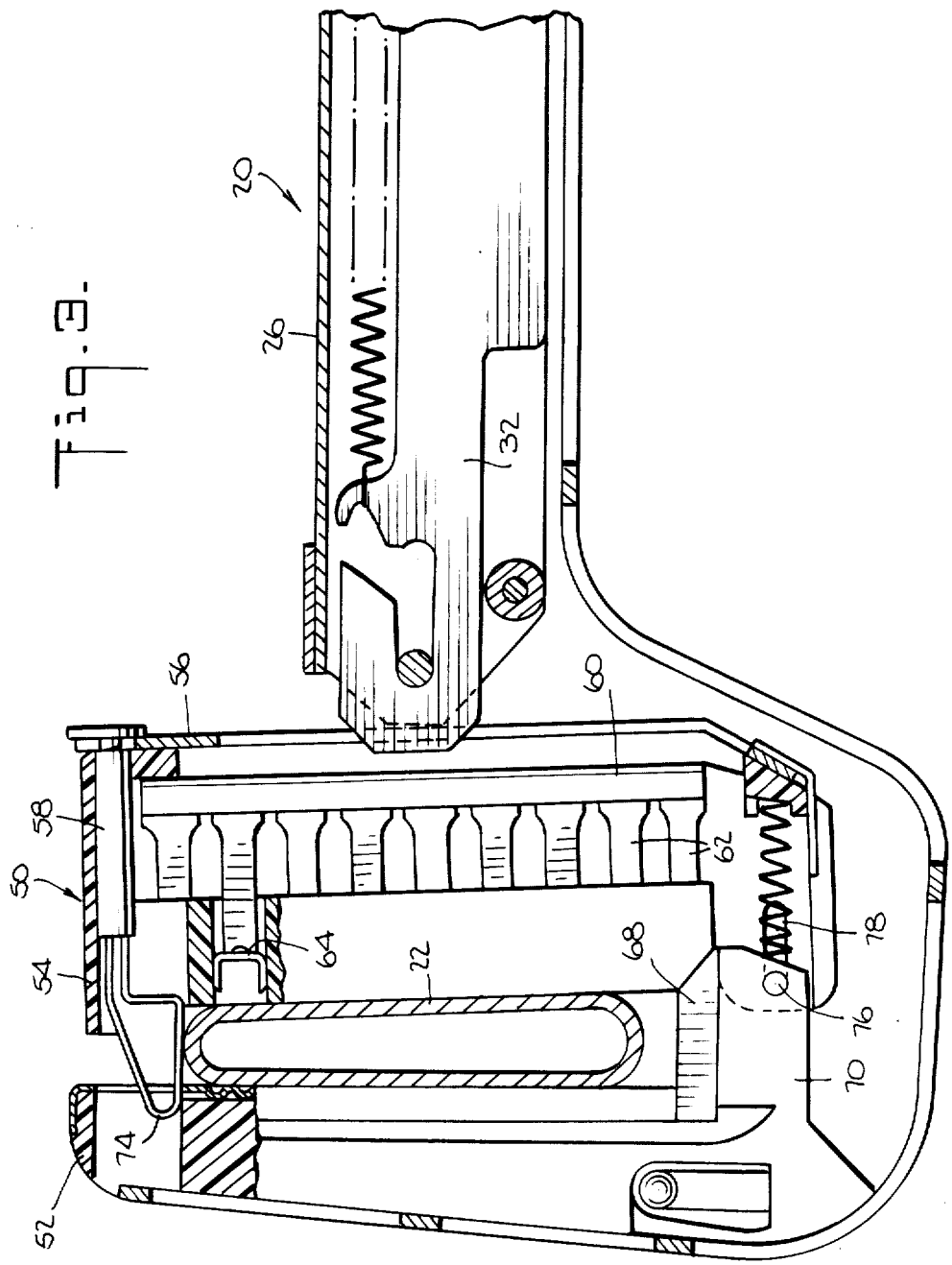

As mentioned above, cartridge 50 is removably mountable in the distal U-shaped portion of actuator 20. With cartridge 50 in place in actuator 20 as shown in FIG. 2, the assembled instrument is positioned relative to the tissue 22 to be fastened so that the anvil part 52 of the cartridge is on one side of the tissue and the fastener holding part 54 of the cartridge is on the other side of the tissue. Clamp actuator 24 is then pivoted clockwise until it is parallel to the proximal-distal axis of actuator 20. This causes clamp pusher 26 to translate in the distal direction, thereby pivoting and translating fastener holding part 54 into tissue clamping relationship with anvil part 52 as shown progressively in FIGS. 3 and 4. Cartridge 50 is constructed so that clamp pusher 26 first compresses leaf spring 56 against the proximal surface of fastener holding part 54 and pivots fastener holding part 54 about pivot pin 76. As shown in FIG. 3, this causes the "upper" end of fastener holding part 54 to initially move toward anvil part 52 before the "lower" end of fastener holding part 54 moves toward the anvil part. In addition, the distal end portion 74 of pin 58 extends distally from the upper end of fastener holding part 54 into anvil part 52 early in the tissue-clamping stroke of the apparatus. Accordingly, the tissue is completely enclosed in the apparatus long before full clamping pressure is applied to the tissue. This prevents any tissue from being extruded from the apparatus when full clamping pressure is subsequently applied to the tissue.

After the tissue has been enclosed in the apparatus as described above, further distal motion of clamp pusher 26 causes fastener holding part 54 to move into substantial parallelism with anvil part 52 so that tissue 22 is fully clamped between parts 52 and 54 as shown in FIG. 4. Pivot pin 76 moves along slots 78 during this phase of the motion of fastener holding part 54. Tissue 22 is now fully clamped and ready to be fastened.

To fasten the tissue, actuator handle 28 is pivoted to the rear. This causes a train of fastener pusher elements 30 and 32 in actuator 20 and 60 and 62 in cartridge 50 to move in the distal direction (see FIG. 5). This in turn drives all of fasteners 64 (which in the depicted embodiment are metal surgical staples) part way through tissue 22 and against anvil 52. Anvil 52 clinches the ends of the legs of staples 64 to fasten the tissue. The fastened tissue is removed from the apparatus by releasing handle 28 and pivoting clamp actuator 24 out of the instrument frame. This proximally retracts clamp pusher 26, thereby allowing fastener holding part 54 to pivot away from anvil part 52 so that tissue 22 can be removed from the apparatus. With clamp actuator 24 pivoted out of the actuator frame, clamp pusher 26 is also pivotable out of the actuator frame as shown in FIG. 1 to facilitate cleaning of the instrument for reuse.

Although fasteners 64 are metal surgical staples in the depicted embodiment, it will be readily apparent to those skilled in the art that two-part resinous fasteners of the general type shown in Green U.S. Pat. No. 4,506,671 could be used instead.

As is best seen in FIGS. 6–8, the depicted embodiment applies fasteners 64 in three parallel rows designated rows 66a, 66b, and 66c, respectively. Outer rows 66a and 66c are somewhat longer than inner row 66b. In accordance with the present invention, to ensure that the edge 22a of tissue 22 adjacent the "lower" end of the fastener array is not beyond that end of the array, cartridge 50 includes a first tissue edge control member 68 which is aligned with inner fastener row 66b and which overlaps or extends into the fastener array between the adjacent ends of outer fastener rows 66a and 66c. In the depicted embodiment, tissue edge control member 68 is a web or rib which projects upwardly from the portion 70 of cartridge 50 which connects fastener holding part 54 and anvil part 52. Web 68 extends parallel to the axis along which fasteners 64 are driven and spans the entire space between the opposing faces of fastener holding part 54 and anvil part 52. In order to allow fastener holding part 54 to move toward anvil part 52 to clamp the tissue, fastener holding part 54 includes a channel 72 for receiving the proximal end of web 68 as part 54 moves toward part 52. Accordingly, at all times during positioning and clamping of tissue 22 in the apparatus, the upper edge of web 68 pushes up on the lower edge 22a of tissue 22. In particular, web 68 pushes the lower edge 22a of tissue 22 up between the lowest fasteners 64 in outer fastener rows 66a and 66c, thereby ensuring that the lower edge of the tissue is not beyond the lower end of the fastener array. The fact that inner fastener row 66b is shorter than outer fastener rows 66a and 66c allows web 68 to thus overlap or project into the fastener array between longer outer fastener rows 66a and 66c.

At the other ("upper") end of the fastener array, the distal end of pin 58 acts as a second tissue edge control member 74. As in the case of web 68, member 74 is aligned with inner fastener row 66b. Prior to operation of clamp actuator 24, member 74 is proximally retracted inside fastener holding part 54 by leaf spring 56 so that it does not interfere with placement of tissue 22 in the apparatus. However, when clamp actuator 24 is operated, member 74 extends from fastener holding part 54 into anvil part 52 in response to compression of leaf spring 56. If the upper edge 22b of tissue 22 is at or near the upper end of the staple array when member 74 is thus extended (see FIG. 7), member 74 pushes that edge of the tissue down between the uppermost fasteners in outer fastener rows 66a and 66c as shown in FIG. 8. Once again, this operation of member 74 is possible because inner fastener row 66b is shorter than outer fastener rows 66a and 66c, thereby allowing member 74 to overlap or extend downwardly into the upper end of the fastener array between the uppermost fasteners in rows 66a and 66c. Member 74 therefore ensures that the upper edge 22b of tissue 22 does not extend beyond the upper end of the fastener array. Together, members 68 and 74 ensure that the fastener array extends completely across tissue 22 and that no portion of the tissue is left unfastened when fasteners 64 are driven.

FIG. 9 shows an alternative embodiment of the invention in which fasteners 64 are applied in four parallel rows 66d, 66e, 66f, and 66g. Outer rows 66d and 66g are longer than inner rows 66e and 66f. Tissue edge control members 80 and 82 are aligned with inner fastener rows 66e and 66f and overlap or extend into each end of the fastener array between the end fasteners in outer fastener rows 66d and 66g. Accordingly, tissue edge control members 80 and 82 prevent the edges of tissue fastened by the depicted array from extending beyond the ends of the array, thereby ensuring that the array extends completely across the tissue and that no portion of the tissue remains unfastened.

FIG. 10 shows another alternative embodiment of the invention in which fasteners 64 are again applied in three parallel rows 66h, 66i, and 66j. In this embodiment, however, inner row 66i is longer than outer rows 66h and 66j. Tissue edge control members 90 and 92 are U-shaped members which partially surround the end fasteners in inner row 66i so that the parallel legs of each U-shaped member overlap or extend into the ends of the fastener array adjacent the ends of outer fastener rows 66h and 66j. Accordingly, tissue edge control members 90 and 92 prevent the edges of tissue fastened by the depicted array from extending beyond the ends of the array, thereby ensuring that the array extends completely across the tissue so that no portion of the tissue can remain unfastened.

It will be understood that the embodiments shown and described herein are only illustrative of the principles of the invention, and that various modifications can be made by those skilled in the art without departing from the scope and spirit of the invention. For example, instead of being embodied in a disposable cartridge for use in a reusable actuator, the entire apparatus could be constructed as a disposable article such as is shown in FIGS. 1–8 of Green U.S. Pat. No. 4,354,628.

What is claimed is:

1. An apparatus for applying a plurality of surgical fasteners to body tissue comprising:
    a fastener holder cartridge containing an array of fastener in parallel rows;
    an anvil opposite said cartridge for clamping of body tissue therebetween;
    a pusher for expelling said array of fasteners from said cartridge towards said anvil part for applying the fasteners to the body tissue; and
    a tissue edge control member at least at one side of said anvil in longitudinal alignment with at least one row of fasteners and extending within said array of fasteners to confine the clamped body tissue within said array of fasteners.

2. An apparatus as set forth in claim 1 wherein said control member is a web projecting from said anvil part.

3. An apparatus as set forth in claim 1 wherein said control member is retractably mounted in said cartridge.

4. An apparatus as set forth in claim 3 wherein said pusher is disposed to expel said control member from said cartridge towards said anvil part.

5. An apparatus as set forth in claim 3 wherein said anvil part has a recess for receiving said control member.

6. An apparatus as set forth in claim 1 wherein said array of fasteners includes a pair of parallel outer rows of fasteners disposed in longitudinal overlapping relation with said control member and at least one inner row of fasteners disposed in longitudinal alignment with said control member.

7. An apparatus as set forth in claim 1 wherein said control member is U-shaped with a pair of legs facing inwardly and said array of fasteners includes a pair of parallel outer rows of fasteners disposed in longitudinal alignment with said legs of said control member and at least one inner row of fasteners disposed in longitudinal overlapping relation with said legs.

8. An apparatus for applying a plurality of surgical fasteners to body tissue comprising:
    a fastener holder cartridge containing an array of fasteners in parallel rows;
    an anvil part opposite said cartridge for clamping of body tissue therebetween;
    a pusher for expelling said array of fasteners from said cartridge towards said anvil part for applying the fasteners to the body tissue; and
    a pair of tissue edge control members longitudinally aligned with said rows at opposite sides of said anvil and extending within said array of fasteners to confine the sides of the clamped body tissue within the array of fasteners.

9. An apparatus as set forth in claim 8 wherein said control members include a web projecting from said anvil part and a retractably mounted control member in said cartridge.

10. An apparatus as set forth in claim 9 wherein said pusher is disposed to expel said control member from said cartridge towards said anvil part.

11. An apparatus as set forth in claim 10 wherein said anvil part has a recess for receiving said control member.

12. An apparatus as set forth in claim 8 wherein said array of fasteners includes a pair of parallel outer rows of fasteners disposed in longitudinal overlapping relation with each of said control members and at least one inner row of fasteners disposed in longitudinal alignment with said control members.

13. An apparatus as set forth in claim 8 wherein each said control member is U-shaped with a pair of legs facing inwardly and said array of fasteners includes a pair of parallel outer rows of fasteners disposed in longitudinal alignment with said legs of each said control member and at least one inner row fasteners disposed in longitudinal overlapping relation with said legs of each control member.

* * * * *

UNITED STATES PATENT AND TRADEMARK OFFICE
CERTIFICATE OF CORRECTION

PATENT NO. : 4,715,520

DATED : December 29, 1987

INVENTOR(S) : William H. Roehr, Jr., et al

It is certified that error appears in the above-identified patent and that said Letters Patent is hereby corrected as shown below:

Column 5, line 16 "fastener" should be -fasteners-
Column 5, line 30 "cer-       should be -car
                  tridge."                tridge-
Column 6, line 42 "row fasteners" should be -row of fasteners- Signed and Sealed this Twenty-eighth Day of June, 1988

Attest:

DONALD J. QUIGG

Attesting Officer

Commissioner of Patents and Trademarks